United States Patent [19]

Jacobsen et al.

[11] Patent Number: 4,477,971
[45] Date of Patent: Oct. 23, 1984

[54] IONTOPHORETIC ELECTRODE STRUCTURE

[75] Inventors: Stephen C. Jacobsen, Salt Lake City; Richard D. Luntz, Murray; Barry K. Hanover, Salt Lake City, all of Utah

[73] Assignee: Motion Control, Inc., Salt Lake City, Utah

[21] Appl. No.: 536,304

[22] Filed: Sep. 27, 1983

Related U.S. Application Data

[62] Division of Ser. No. 319,074, Nov. 6, 1981, Pat. No. 4,419,092.

[51] Int. Cl.³ .......................................... H01R 43/02
[52] U.S. Cl. .................................................. 29/877
[58] Field of Search ................. 29/877; 204/403, 414, 204/415, 435; 128/639, 640, 641, 635

[56] References Cited

U.S. PATENT DOCUMENTS

| | | | |
|---|---|---|---|
| 3,580,240 | 5/1971 | Cosentino | 128/640 |
| 3,623,479 | 11/1971 | Day | 128/639 |
| 4,114,263 | 9/1978 | Szpur | 29/877 |
| 4,166,457 | 9/1979 | Jacobsen et al. | 128/639 |
| 4,250,878 | 2/1981 | Jacobsen et al. | 604/20 |
| 4,273,134 | 6/1981 | Ricciardelli | 204/415 X |
| 4,416,274 | 11/1983 | Jacobsen et al. | 604/20 |

FOREIGN PATENT DOCUMENTS

| | | | |
|---|---|---|---|
| 808463 | 3/1969 | Canada | 206/219 |
| 2737665 | 3/1979 | Fed. Rep. of Germany | 128/640 |

*Primary Examiner*—Howard N. Goldberg
*Assistant Examiner*—Carl J. Arbes
*Attorney, Agent, or Firm*—Thorpe, North & Western

[57] ABSTRACT

An iontophoretic bioelectrode includes an enclosure having a bottom wall formed of a membrane through which ions may migrate when subjected to an electric field, and an upper wall joined to the bottom wall to define an interior compartment for holding an ion-containing solution. An electrode in the form of the male portion of a conventional clothing snap is mounted to the enclosure to communicate electrically with solution contained in the interior compartment. A needle receiving element is mounted in the upper wall of the enclosure. This element is in the form of a section of conduit having a receiving end, which is directed upwardly, and a blocking end which includes a platform for preventing a needle inserted into the receiving end from passing all the way through the conduit. A resilient plug is disposed in the receiving end of the conduit to prevent solution from escaping from the interior compartment. The plug is formed of a material through which a needle may be inserted but which, when the needle is retracted, closes about the opening made by the needle to prevent the escape of solution.

1 Claim, 4 Drawing Figures

IONTOPHORETIC ELECTRODE STRUCTURE

This application is a division of application Ser. No. 319,074, filed 11/6/81, now U.S. Pat. No. 4,419,092 issued 12/6/83.

BACKGROUND OF THE INVENTION

This invention relates to a new and improved iontophoretic bioelectrode structure which is simple in design, and to a method of manufacturing the structure.

Iontophoresis is a technique of delivering ions into a person's skin or tissue by placing a solution or other medium containing the ions in contact with the skin, and applying electric current to the medium. The solution or medium containing the ions is typically carried by a first bioelectrode pouch or receptacle. Ions are caused to migrate from the ion carrying medium through the skin or tissue by the application of the electric current to the medium, and by placement against the skin and of a second bioelectrode within proximity of the first bioelectrode and the application of current of opposite polarity to the second bioelectrode. This technique has been discussed in a number of prior art patents including U.S. Pat. Nos. 4,141,359 and 4,166,457. Examples of bioelectrodes which are generally useful for making electrical contact with the skin are described in U.S. Pat. Nos. 3,862,633, 3,945,384 and 3,973,557.

There have been several bioelectrode proposals for carrying the ion solution or medium and placing it in proximity with the skin including provision of a receptacle with a wetable barrier on one side thereof. The wetable barrier or wall is covered until time of use and then uncovered for placement against the skin. Then, upon application of the electrical current, the ions migrate through the wall into the skin.

Another proposed arrangement involves the use of a receptacle having a microporous membrane on one side thereof which may be placed in contact with a person's skin. The membrane is selected so that it will not leak prior to use, but will allow migration of ions therethrough to the skin upon application of an electric current to the ion-carrying solution. With this arrangement, less care need be given to storage, transport, or use of the receptacle since the ion containing fluid will not leak as it is used.

Still another suggested arrangement involves a bioelectrode structure which includes a holder for holding ions to be delivered, wherein the holder is adapted to inhibit movement of ions in a direction generally parallel to the surface of the skin or tissue while allowing movement toward the skin or tissue. One exemplary configuration of this bioelectrode is to provide the receptacle with a gel material preloaded with ions.

Generally, bioelectrodes heretofore proposed either provide for including the ion-containing solution in the bioelectrode as it is manufactured, or simply providing a structure into which ion-containing solution can later be introduced by the user. In the latter case, typically a special structure is provided on the bioelectrode for receiving a solution applicator, and a special applicator structure is provided for supplying the solution to the bioelectrode. Such special structure is employed, among other things, to enable introduction of solution into the bioelectrode without puncturing it.

SUMMARY OF THE INVENTION

It is an additional object of the invention to provide a new and improved method of manufacturing bioelectrodes.

The above and other objects of the invention are realized in a bioelectrode structure and method of manufacturing same. The bioelectrode includes an enclosure having a bottom wall formed of a membrane through which ions may migrate when subjected to an electric field, and an upper wall joined to the bottom wall to define an interior compartment for holding an ion-containing solution. An electrode is mounted to the enclosure to communicate electrically with the interior thereof through the upper wall. A receptacle element is disposed in the enclosure for receiving a needle or similar solution-introducing device and for thereafter transferring the solution to the interior of the enclosure.

One embodiment of the receptacle element is in the form of a conduit open at both ends and having a first end which is directed away from the bottom wall of the enclosure. A blocking element is disposed at the second end of the conduit to prevent the needle inserted into the conduit through the first end from passing through the second end, while also allowing fluid to flow through the conduit and out the second end. A plug is positioned in the first end of the conduit to prevent solution from escaping from the interior compartment of the enclosure but for allowing penetration by a needle.

Another embodiment of the receptacle element is also in the form of a conduit open at one end only, with narrow openings on the sides of the conduit for allowing the flow therethrough of fluid.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
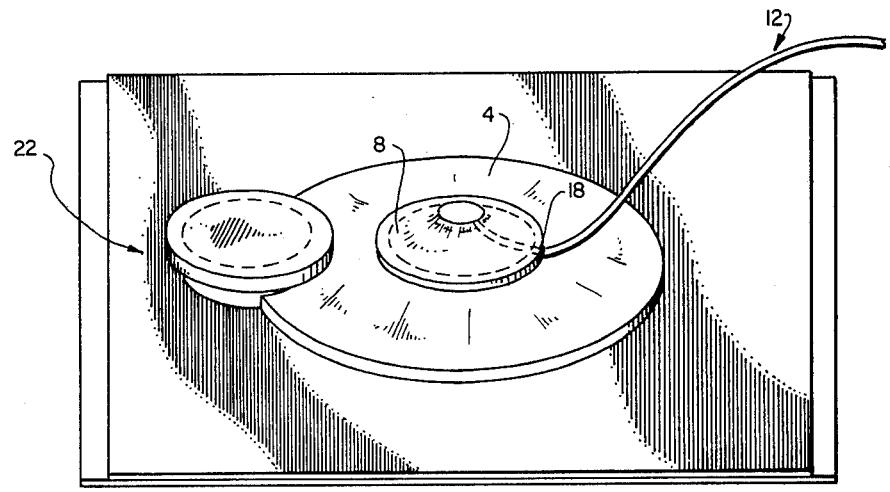
FIG. 1 is a perspective view of a bioelectrode made in accordance with the principles of the present invention.
Figure 2:
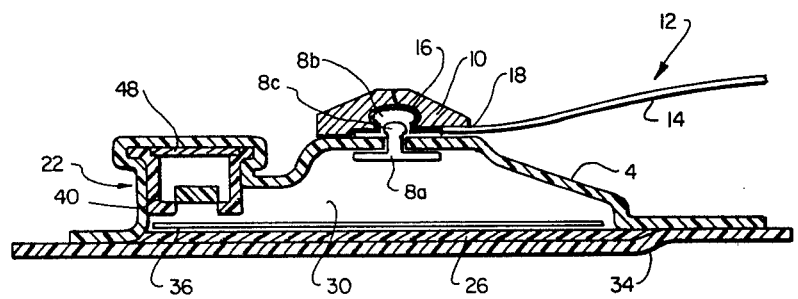
FIG. 2 is a side, cross-sectional view of the bioelectrode of FIG. 1.

Referring to FIGS. 1 and 2, there is shown a bioelectrode composed of a generally dome-shaped upper wall 4 which may be made of plastic, polyvinyl chloride, polyurethane, or other material suitable for holding a solution. Attached to the wall 4 to be exposed to the area under the wall is a male element 8 of a conventional metallic snap used on clothing and the like. The element 8 includes a base portion 8a and an upper or nipple portion 8b projecting upwardly from the base portion when the two are snapped together. The base portion 8a includes an upstanding stud 8c which is fitted through an opening in the wall 4 and is received into a receptacle formed in the underneath side of the nipple portion 8b. When snapped together as shown in FIG. 2, the two portions 8a and 8b are held in place in the wall 4 so that the base portion 8b is exposed to a compartment 30, to be discussed momentarily. A dome-shaped cover 10 is provided to fit over the nipple 8b, and disposed to extend between the cover and the nipple is a wire conductor 12, one end of which has insulation material 14 removed to expose bare wire 16. The conductor 12 exits from under the cover 10 through a slot 18 in the cover 10. The exposed wire 16 of the conductor 12 is disposed between the nipple 8b and the cover 10 to make electrical contact with the nipple. The cover 10 may be made of plastic or other resilient material.

The other end of the conductor 12 would be connected to an electrical potential source (not shown).

Also attached to the underneath side of the upper wall 4 is a receptacle structure 22 through which ion-containing solution is introduced into the bioelectrode of FIGS. 1 and 2. This structure will be described momentarily.

The bioelectrode of FIGS. 1 and 2 also includes a bottom wall 26 whose perimeter is joined to the upper wall 4 to define an interior compartment 30 for holding an ion containing solution. The bottom wall 26 comprises a membrane which will allow the migration of ions therethrough when an ion-containing solution in the compartment 30 is subjected to an electric field (such as when an electrical potential is applied to the conductor 12). An exemplary material for use as the bottom wall 26 is a polycarbonate semipermeable membrane. The material selected for the bottom wall 26 may differ for different ion-containing solutions to be used in the bioelectrode. For example, polycarbonate materials of differing pore sizes, other hydrophilic or hydrophobic materials such as foams made from acrylic copolymers, polyvinyl chloride copolymers or cellulosics might also be used depending upon the type of solution to be used.

A protective cover 34 is secured by a releasable adhesive to the bottom wall 26 and to the bottom surface of a portion of the upper wall 4 to prevent damage or contamination to the bottom wall. This material could be simple plastic, treated paper, or other suitable covering material. A piece of filter paper 36 is placed in the compartment 30 above the bottom wall 26 to protect the wall 26 during production and shipping.

As indicated earlier, the receptacle 22 is positioned in the bioelectrode to allow introduction of ion-containing solution into the interior compartment 30. One embodiment of the receptacle 22 (shown in FIGS. 2 and 3) includes a generally annular conduit 40, an upper end of which is formed with an outwardly and upwardly flaring lip 42. The lip 42 is formed to define a seat 44 on which is placed a plug 48. The plug 48 is made of a resilient material through which a hypodermic needle may be inserted but which will close about the opening made by the needle when the needle is removed. The function of the plug 48 is to prevent the leaking of solution through the conduit 40 from the interior compartment 30. An exemplary material for the plug 48 is natural rubber, silicone rubber, butyl rubber, etc.

The bottom end of the conduit 40, like the upper end thereof, is also open to allow transmission therethrough of an ion-containing solution. Formed in the bottom end is a blocking structure for preventing a hypodermic needle inserted into the conduit through the upper end from passing all the way through the conduit and out the bottom end. The blocking structure includes a platform 52 disposed within the conduit, with the perimeter thereof being spaced from the interior wall of the conduit to allow solution to flow thereby. A circumferential lip 56 projects inwardly from the bottom of the conduit 40 to define a ledge 58 positioned below the periphery of the platform 52. Legs 62 project upwardly from the lip 56 to contact and support the bottom of the platform 52. The legs 62 are spaced about an opening 64 defined by the inward termination of the lip 56.

Figure 3:
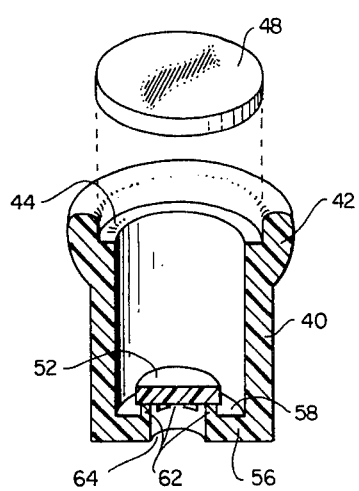
FIG. 3 is a perspective, cross-sectional view of one embodiment of the receptacle of the bioelectrode of FIG. 1.

As can best be seen from FIG. 3, solution is introduced through the conduit 40 by inserting a hypodermic needle into the plug 48 and then discharging the solution through the hypodermic needle so that it flows past the perimeter of the platform 52, through the spaces between the legs 62, and out the opening 64 to the interior compartment 30 of the bioelectrode (FIG. 2). The hypodermic needle is prevented from being inserted all the way through the conduit 40 by the platform 52 and the ledge 58. If the hypodermic needle slips past the platform, then it will contact and be stopped by the ledge 58.

Figure 4:
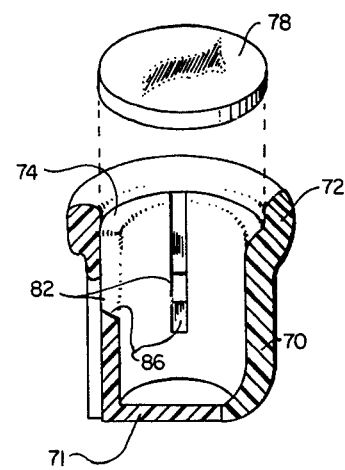
FIG. 4 is a perspective, cross-sectional view of another embodiment of the receptacle.

An alternative embodiment of the receptacle 22 of FIG. 1 is shown in FIG. 4. This embodiment includes an annular conduit or vessel 70, the bottom end of which is closed with a bottom wall 71, and the upper end of which is open and is formed with an outwardly and upwardly flaring lip 72. The lip 72 defines a seat 74 on which is placed a plug 78, similar to the embodiment of FIG. 3. This plug is made of a resilient material through which a hypodermic needle may be inserted, and which will close about the needle-created opening when the needle is removed. Formed in the side walls of the vessel 70 are a plurality of openings 82 which are moderately narrower than the diameter of a hypodermic needle. The openings 82 are formed so that each opening or window sill 86 slopes downwardly and inwardly to deflect to the interior vessel any needle which may contact the sill. This structure, as with that of FIG. 3, prevents a needle inserted thereinto from passing all the way through the structure since the needle will contact and be stopped by the bottom wall 71.

It should be understood that there may be a variety of blocking structure configurations to prevent a hypodermic needle from being inserted all the way through the receptacle 22. It is desirable, of course, to provide such a blocking feature so that the hypodermic needle does not puncture other parts of the bioelectrode.

Referring again to FIG. 2, the receptacle 22 is disposed in the upper wall 4 of the bioelectrode so that the bottom of the receptacle is out of contact with the bottom wall 26. By being spaced above the bottom wall 26, the solution introduced into the bioelectrode may more readily flow from the receptacle 22 to fill the interior compartment 30. If the receptacle 22 were positioned just above or in contact with the bottom wall 26, then the likelihood of a concentration of the solution at that site would be increased and this, in turn, might increase the chance of burning of the skin or tissue of the person when the bioelectrode were placed in use. This is because the solution would be concentrated at the location of the receptacle 22.

The structure described in connection with FIGS. 1-4 is simple in construction and thus may be readily manufactured. An exemplary method of manufacturing the bioelectrode includes the steps of placing a plug 48 and conduit 40 onto a mold whose upper surface is formed into a dome shape similar to the shape of the upper wall 4, and then placing a section of plastic polyvinyl chloride, polyurethane, etc., material over the mold, plug and conduit. The material is then vacuum formed over the mold, plug and conduit to the shape of the mold. When removed from the mold, the plug and conduit remain attached to the underneath side of what will be the upper wall of the bioelectrode. The base portion 8a and nipple portion 8b of the snap 8 are then attached to the upper wall 4. The exposed part 16 of the conductor 12 is then positioned over the nipple 8b and the cover 10 is placed over the nipple and held in place with a suitable adhesive. The filter paper 36 is placed in the compartment 30 and the bottom wall 26 is attached at or near its periphery to the upper wall 4. The protective cover 34 is then put in place in contact with the bottom wall 26 and a portion of the upper wall 4.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A method of producing a bioelectrode comprising the steps of placing a hollow conduit with a resilient plug fitted in the top thereof onto a mold whose upper surface is generally dome shaped, the lower end of the conduit including a blocking element which prevents a needle from passing all the way through the conduit, said conduit including openings which allow ion-containing solution to flow therethrough from the conduit, placing a piece of vacuum formable material over the hollow conduit, plug and mold, vacuum forming the material to the shape of the mold with the hollow condit and plug thereon, removing the material and hollow conduit and plug from the mold, attaching a conductive element to the material so that a first portion of the element is exposed to the area underneath the material and a second portion is exposed to the area above the material, placing a cover of resilient material over the second portion of the conductive element, with one end of an electrical conductor sandwiched between the cover and second portion, joining a membrane to the perimeter of the material to define an interior compartment between the membrane and the material, said membrane being adapted to allow the migration of ions therethrough when an ion-containing solution in the interior compartment is subjected to an electric field, and placing a protective cover over the underneath sides of the material and membrane.

* * * * *